United States Patent

Yale et al.

[11] 4,004,016
[45] Jan. 18, 1977

[54] AMINO-BENZIMIDAZOLE DERIVATIVES

[75] Inventors: Harry L. Yale, New Brunswick; James A. Bristol, Boonton, both of N.J.

[73] Assignee: E. R. Squibb & Sons, Inc., Princeton, N.J.

[22] Filed: Aug. 11, 1975

[21] Appl. No.: 603,484

[52] U.S. Cl. .............................. 424/273; 260/309.2
[51] Int. Cl.[2] ............ C07D 235/32; A61K 31/415
[58] Field of Search ................. 260/309.2; 424/273

[56] References Cited

UNITED STATES PATENTS 3,399,212  8/1968  Hoover et al. ............... 260/309.2
3,401,173  9/1968  Chow et al. .................. 260/309.2

OTHER PUBLICATIONS

Bednyagina et al., Chem. Abst. 1961, vol. 55, Cols. 1586–1587.
Filipskikh et al., Chem. Abst. 1972, vol. 77, No. 88401e.
Jensen et al., J. Med. Chem. 1970, vol. 13, pp. 1043–1047.
Pozharskii et al., I Chem. Abst. 1971, vol. 75, No. 48982x.
Pozharskii et al., II Chem. Abst. 1972, vol. 76, No. 15367u.
Simonov et al., I Chem. Abst. 1961, vol. 55, Col. 16520.
Simonov et al., II Chem. Abst. 1963, vol. 58, Col. 9048.
Simonov et al., III Chem. Abst. 1967, vol. 67, No. 82160x.
Chemical Abstracts Chemical Substance Index (A–D), 1972, vol. 76, p. 518CS, Col. 1.

Primary Examiner—Natalie Trousof
Attorney, Agent, or Firm—Lawrence S. Levinson; Merle J. Smith; Burton Rodney

[57] ABSTRACT

Amino-benzimidazole derivatives of the structure

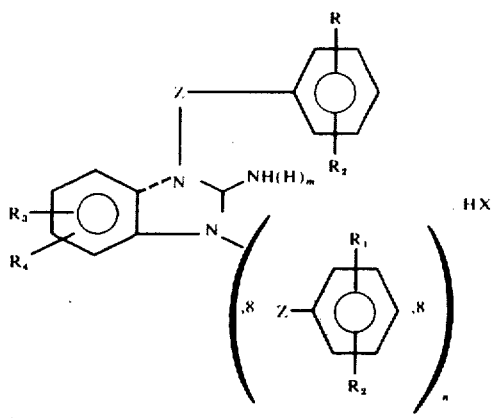

are provided which are useful as anti-inflammatory agents. In addition, a method for preparing such compounds, pharmaceutical compositions containing such compounds, and methods for using such pharmaceutical compositions in the treatment of inflammation are taught.

20 Claims, No Drawings

AMINO-BENZIMIDAZOLE DERIVATIVES

This invention relates to compounds of the formula

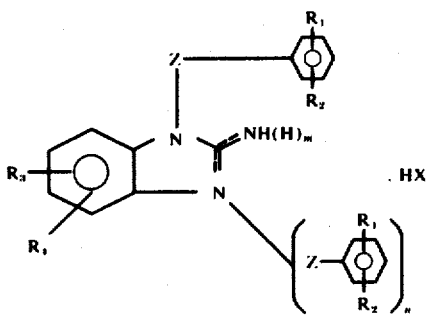

wherein
Z is straight or branched chain alkylene containing from 1 to 4 carbons;
$R_1$ and $R_2$ are the same or different and may be hydrogen, halo, lower alkyl, lower alkoxy, trifluoromethyl, or N,N-dimethylsulfonamido;
$R_3$ and $R_4$ are the same or different and may be hydrogen, lower alkyl, lower alkoxy, aryl, halo, aralkyl, or substituted aryl;
X is Cl, Br or I;
m is 0 or 1;
and n is 0 or 1;
One of "====" represents a single bond while the other "====" represents a double bond; thus where m is 1, the "====" linking $NH_2$ to the ring carbon is a single bond and n is 0 so that the "====" linking N and C ring atoms is a double bond; where m is 0, n is 1, the "====" linking NH to the ring carbon is a double bond and the other "====" linking the N and C ring atoms is a single bond.

Thus, the compounds of the invention include compounds of formulae II and III as set out below.

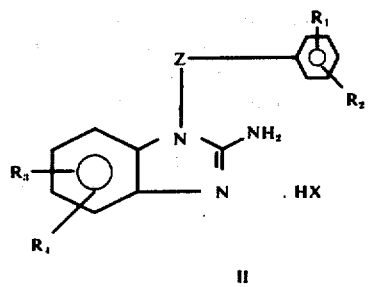

II

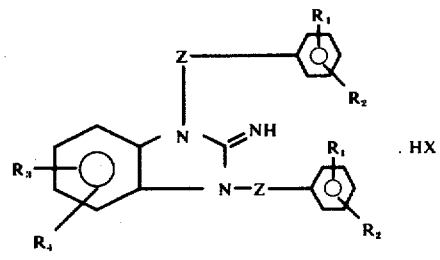

III

The alkylene group represented by Z includes straight chain groups containing 1 to 4 carbons, namely $-CH_2-$, $-CH_2CH_2-$, $-CH_2CH_2CH_2-$ and $-CH_2CH_2CH_2CH_2-$, and branched chain groups containing 1 to 4 carbons, such as

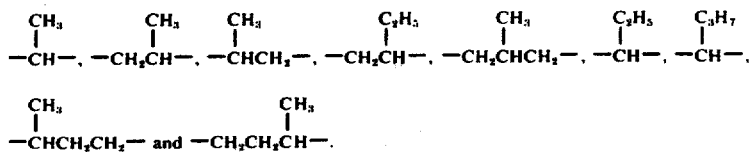

The lower alkyl groups represented by the above $R_1$, $R_2$, $R_3$ and $R_4$ groups include straight or branched chain aliphatic hydrocarbon radicals having up to seven carbon atoms, such as methyl, ethyl, propyl, isopropyl, butyl, isobutyl, t-butyl, amyl, hexyl, heptyl and the like.

The alkoxy group includes straight and branched chain radicals of up to and including seven carbon atoms, corresponding to the above alkyl groups, e.g., methoxy, ethoxy, propoxy, isopropoxy and the like.

The term "halo" includes each of the four halogens but bromine and chlorine are preferred.

The term "aryl" includes monocyclic or bicyclic monovalent aromatic ring systems such as phenyl or naphthyl. These aryl radicals can include as substituents any of the $R_1$ or $R_2$ groups mentioned hereinbefore.

The term "aralkyl" encompasses a lower alkyl group as defined above substituted with an aryl group as defined above, such as benzyl or phenethyl.

In preferred embodiments of the invention, $R_1$ and $R_2$ are hydrogen, halo, lower alkyl, lower alkoxy and trifluoromethyl; hydrogen, halo, lower alkyl and lower alkoxy; hydrogen, halo and lower alkyl; and $R_3$ and $R_4$ can be hydrogen, lower alkyl and halo.

The preferred compounds of the invention are those where Z is $-CH_2-$, $-CH_2CH_2-$, or $-CH_2CH_2CH_2-$, $R_1$ is halo and $R_2$ is hydrogen, $R_3$ and $R_4$ are hydrogen, and m is 0 and n is 1 or m is 1 and n is 0.

In addition, in accordance with the present invention, a method is provided for preparing compounds of the present invention (I) by reacting a 2-aminobenzimidazole of the structure

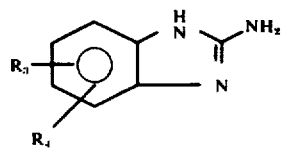

IV wherein $R_3$ and $R_4$ are as defined above, with a phenylalkyl halide of the formula

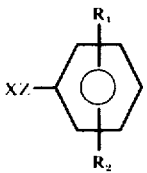

wherein X, Z, R₁ and R₂ are as defined above.

The above reaction is carried out under anhydrous conditions in the presence of one or more of a variety of solvents such as sulfolane (tetramethylsulfone), or aromatic solvents such as toluene, xylene, diethylbenzene, cumene, or trimethylbenzene, with sulfolane being preferred. In addition, it is preferred that each of the compounds (IV) and (V) be separately dissolved in the same solvent before they are admixed with one another.

The temperatures and reaction times employed in carrying out the above reaction may range from 0° to 150° C for periods of about 1 hour to 10 days, and preferably from about 40° to about 100° C for 1 to 10 days where sulfolane is employed as the solvent, and from about 80° to about 150° C for 1 to 24 hours where an aromatic solvent is employed.

The molar ratio of the 2-aminobenzimidazole (IV) to the phenylalkyl halide (V) can range from about 1:8 to about 1:1 and preferably from about 1:3 to about 1:1, and optimally 1:2 or 1:1.

The reaction mixture obtained from the above reaction will include compounds of formulas II and III. The formula III compound may easily be separated from such mixture by cooling the mixture, and optionally drying and dissolving in solvent, such as acetonitrile, to form crystals of the formula III compound. The filtrate from the above reaction mixture can then be concentrated to dryness, and the resulting residue washed, stirred in boiling water, cooled, and the solid filtered out to give more of the formula III compound. The aqueous filtrate is then concentrated to dryness and the residual solid is recrystallized to give the formula II compound.

The preparation of a variety of 2-aminobenzimidazoles which may be employed as starting materials herein is well documented in Weissberger's "The Chemistry of Heterocyclic Compounds, Imidazole and Its Derivatives", Interscience Publishers Co., New York, 1953.

It will be understood that unsubstituted 2-aminobenzimidazoles (IV), that is where R₃ and R₄ are hydrogen, can be employed to form compounds of formulae II and III, and thereafter other R₃ and/or R₄ radicals may be inserted in the 2-aminobenzimidazole ring in place of one or two hydrogens, employing conventional procedures as will be apparent to one skilled in the art.

The phenylalkyl halides (III) can be prepared as described in the paper entitled "Novel Polycyclic Heterocycles. XI" by R. B. Petigara et al., Journal of Heterocyclic Chemistry, 11, 331 (1974).

The compounds II and III of this invention have been found to be useful as antiinflammatory agents in mammals, such as rats, mice, dogs and the like as indicated by passive cutaneous anaphylaxis is the rat [Ref: Ovary, Z and Bier, O.G. Proc. Soc. Exp. Biol. Med. 81: 584, 1952, Goose, J. and Blair, A. M. J. N., *Immunology*, 16: 749, 1969], when administered in amounts ranging from about 1.2 mg to about 30 mg. per kg. of body weight per day. A preferred dosage regimen for optimum results would be from about 1.5 mg. to about 15 mg. per kg. of body weight per day, and such dosage units are employed that a total of from about 100 mg. to about 2 g. of active ingredient for a subject of about 70 kg body weight is administered in a 24 hour period.

The compounds of the present invention in the described dosages are intended to be administered orally; however, other routes such as rectally, intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5 to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 10 and 200 milligrams of active compound.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The invention will be described in greater detail in conjunction with the following specific examples.

The following examples are provided for illustrative purposes and may include particular features of the invention; however, the examples should not be construed as limiting the invention, many variations of which are possible without departing from the spirit or scope thereof. All temperatures are on the Centigrade scale.

EXAMPLE 1

1,3-Dihydro-1,3-bis[2-(o-bromophenyl)ethyl]-2H-benzimidizol-2-imine Hydrobromide and
2-Amino-1-[2-(o-bromophenyl)ethyl]-benzimidazole Hydrobromide A solution of 5.5 g of 2-aminobenzimidazole and 11.0 g of 2-(o-bromophenyl)ethyl bromide in 250 ml of xylene is heated in a nitrogen atmosphere under reflux for 18 hours. The reaction mixture is cooled and the crystals that separate are filtered and dried. This product weighs 3.7 g and is recrystallized from acetonitrile to give 3.4 g of 1,3-dihydro-1,3-bis[2-(o-bromophenyl)ethyl]-2H-benzimidazol-2-imine hydrobromide, m.p. 248°–249°.

The xylene filtrate from the above product is concentrated to dryness and the residue is washed thoroughly with small portions of hexane to give a granular residue that weighs 4.6 g. This solid is stirred with 160 ml of boiling water and the suspension allowed to cool to ambient temperature. The solid is filtered to give 1.2 g of the above product, m.p. 248°–249°. The aqueous filtrate is concentrated to dryness and the residual solid, 3.2 g, is recrystallized from butyronitrile to give 2.8 g of 2-amino-1-[2-(o-bromophenyl)ethyl]benzimidazole hydrobromide, m.p. 196°–198°.

EXAMPLE 2

1,3-Dihydro-1,3-bis(2-phenylethyl)-2H-benzimidazol-2-imine Hydrobromide and
2-Amino-1-(2-phenylethyl)benzimidazole Hydrobromide A mixture of 13.3 g of 2-aminobenzimidazole, 18.5 g of 2-phenylethyl bromide, and 300 ml of xylene is heated as in Example 1. Subsequently, the solution is concentrated to dryness, the residue is dissolved in boiling acetonitrile, and clarified by filtration. The crystalline product that separates in the cooled filtrate is filtered to give 6.8 g of 1,3-dihydro-1,3-bis(2-phenylethyl)-2H-benzimidazol-2-imine hydrobromide, m.p. 259°–260°.

The acetonitrile filtrate from the 6.8 g is concentrated to one-half its original volume and the residual liquid is allowed to cool to ambient temperature. The crystalline solid that separates is filtered to give an additional 2.4 g of solid, m.p. 259°–260°, identical in all respects with the above product.

The acetonitrile filtrate from the above 2.4 g is concentrated to dryness and the residue, 6.6 g, is stirred with 200 ml of boiling water and then allowed to cool to ambient temperature. The solution is clarified by filtration from 0.4 g of the above bis-compound, and the filtrate is concentrated to dryness. The residual solid, 6.1 g is recrystallized from butyronitrile to give 5.1 g of 2-amino-1-(2-phenylethyl)benzimidazole hydrobromide, m.p. 206°–208°.

EXAMPLE 3

1,3-Dihydro-1,3-bis(2-phenylethyl)-2H-benzimidazol-2-imine Hydrobromide and
2-Amino-1-(2-phenylethyl)benzimidazole Hydrobromide A solution of 9.0 g of 2-aminobenzimidazole, 26.5 g of 2-phenethyl bromide, and 25 ml of sulfolane is heated on the steam bath for 5.75 hours, cooled to 60° and diluted with 50 ml of acetonitrile. Further cooling to ambient temperature gives a heavy precipitate. This solid is filtered and washed with 10 ml of cold acetonitrile to give 12.3 g of dry solid. This solid is added to 360 ml of boiling water, the whole agitated for 5 minutes and allowed to cool to ambient temperature. The solid is filtered and dried to give 5.2 g of 1,3-dihydro-1,3-bis(2-phenylethyl)-2H-benzimidazol-2-imine hydrobromide, m.p. 259°–260°, after recrystallization from acetonitrile.

The aqueous filtrate from the above product is concentrated to dryness to give 6.4 g of solid. This is recrystallized from butyronitrile to give 5.3 g of 2-amino-1-(2-phenylethyl)benzimidazole hydrobromide, m.p. 206°–208°.

EXAMPLE 4

1,3-Dihydro-1,3-bis(o-bromobenzyl)-2H-benzimidazol-2-imine Hydrobromide and
2-Amino-1-(o-bromobenzyl)benzimidazole Hydrobromide A solution of 25.0 g of o-bromobenzyl bromide, 13.4 g of 2-aminobenzimidazole, and 50 ml of sulfolane is kept at an internal temperature of 60° for 8 hours, cooled to ambient temperature, and diluted with 100 ml of anhydrous ether. The mixture is then kept at 0° for 24 hours and the crystalline solid filtered and dried to give 26.4 g of material. This is dissolved in acetonitrile, at reflux temperature, and the hot solution clarified by filtration. The filtrate is allowed to cool to ambient temperature, then chilled at 0°. The solid that separates is filtered to give 16.2 g of 1,3-dihydro-1,3-bis(o-bromobenzyl)-2H-benzimidazol-2-imine hydrobromide. The acetonitrile filtrate is concentrated to one-half its volume and the residual liquid cooled to ambient temperature to give an additional 3.4 g of the above bis-compound. The acetonitrile filtrate from the 3.4 g is concentrated to dryness and the residue recrystallized from butyronitrile to give 6.6 g of 2-amino-1-(o-bromobenzyl)benzimidazole hydrobromide.

EXAMPLE 5

1,3-Dihydro-1,3-bis[3-(p-chlorophenyl)propyl]-2H-benzimidazol-2-imine Hydroiodide and
2-Amino-1-[3-(p-chlorophenyl)propyl]-benzimidazole Hydroiodide A solution of 14.1 g of 3-(p-chlorophenyl)propyl iodide, 6.8 g of 2-aminobenzimidazole and 25 ml of sulfolane is heated as in Example 3. Workup as described in Example 4, involving the use of acetonitrile as the separation solvent results in the isolation of the name compounds.

EXAMPLE 6

1,3-Dihydro-1,3-bis[(m-chlorophenyl)methyl]-2H-benzimidazol-2-imine Hydrobromide and
2-Amino-1-[2-(m-chlorophenyl)-methyl]benzimidazole Hydrobromide Following the procedure of Example 1 and replacing 2-(o-bromophenyl)ethyl bromide with m-chlorophenylmethyl bromide, the title compounds are obtained.

EXAMPLE 7

1,3-Dihydro-1,3-bis[4-(p-methylphenyl)butyl]-2H-benzimidazol-2-imine Hydrochloride and 2-Amino-1-[4-(p-methylphenyl)butyl]-benzimidazole Hydrochloride Following the procedure of Example 2 and replacing 2-phenylethyl bromide with 4-(p-methylphenyl)butyl chloride, the title compounds are obtained.

EXAMPLE 8

1,3-Dihydro-1,3-bis[2-(o-ethoxyphenyl)ethyl]-2H-benzimidazol-2-imine Hydrochloride and 2-Amino-1-[2-(o-ethoxyphenyl)-ethyl]benzimidazole Hydrochloride Following the procedure of Example 3 and replacing 2-phenethyl bromide with 2-(o-ethoxyphenyl)ethyl chloride, the title compounds are obtained.

EXAMPLE 9

1,3-Dihydro-1,3-bis[3-[m-(trifluoromethyl)phenyl]-propyl]-2H-benzimidazol-2-imine Hydroiodide and 2-Amino-1-[3-[m-(trifluoromethyl)phenyl]propyl]-benzimidazole Hydroiodide Following the procedure of Example 4 and replacing o-bromobenzyl iodide with 3-[m-(trifluoromethyl)-phenyl]-propyliodide, the title compounds are obtained.

EXAMPLE 10

1,3-Dihydro-1,3-bis[2-(p-N,N-dimethylsulfonamidophenyl)-ethyl]-2H-benzimidazol-2-imine Hydrobromide and 2-Amino-1-[2-(p-N,N-dimethylsulfonamidophenyl)ethyl]benzimidazole Hydrobromide Following the procedure of Example 2 and replacing 2-phenylethyl bromide with 2-(p-N,N-dimethylsulfonamidophenyl)ethylbromide, the title compounds are obtained.

EXAMPLE 11

1,3-Dihydro-1,3-bis[(2-bromo-4-methylphenyl)methyl]-2H-benzimidazol-2-imine Hydrobromide and 2-Amino-1-(2-bromo-4-methylphenyl)methylbenzimidazole Hydrobromide Following the procedure of Example 2 and replacing 2-phenylethyl bromide with 2-bromo-4-methylphenylmethyl bromide, the title compounds are obtained.

EXAMPLE 12

1,3-Dihydro-1,3-bis[2-(3-fluoro-4-t-butylphenyl)ethyl]-2H-benzimidazol-2-imine Hydrobromide and 2-Amino-1[2-(3-fluoro-4-t-butylphenyl)ethyl]benzimidazole Hydrobromide Following the procedure of Example 2 and replacing 2-phenylethyl bromide with 2-(3-fluoro-4-t-butylphenyl)ethyl bromide, the title compounds are obtained.

EXAMPLE 13

1,3-Dihydro-1,3-bis[3-(4-chloro-3-n-propoxyphenyl)-propyl]-2H-benzimidazol-2-imine Hydrobromide and 2-Amino-1-[3-(4-chloro-3-n-propoxyphenyl)propyl]-benzimidazole Hydrobromide Following the procedure of Example 2 and replacing 2-phenylethylbromide with 3-(4-chloro-3-n-propoxyphenyl)-propyl bromide, the title compounds are obtained.

EXAMPLE 14

1,3-Dihydro-1,3-bis[4-(2-ethyl-5-methoxyphenyl)-butyl]-2H-benzimidazol-2-imine Hydrobromide and 2-Amino-1-[4-(2-ethyl-5-methoxyphenyl)butyl]benzimidazole Hydrobromide Following the procedure of Example 2 and replacing 2-phenylethyl bromide with 4-(2-ethyl-5-methoxyphenyl)butyl bromide, the title compounds are obtained.

EXAMPLE 15

1,3-Dihydro-1,3-bis[3-[2-bromo-4-(trifluoromethyl)-phenyl]-propyl]-2H-benzimidazol-2-imine Hydrochloride and 2-Amino-1-[3-[2-bromo-4-(trifluoromethyl)phenyl]-propyl]benzimidazole Hydrochloride Following the procedure of Example 2 and replacing 2-phenylethyl bromide with 3-[2-bromo-4-(trifluoromethyl)-phenyl]propyl chloride, the title compounds are obtained.

EXAMPLE 16

1,3-Dihydro-1,3-bis[(3-chloro-4-N,N-dimethylsulfonamidophenyl)methyl]-2H-benzimidazol-2-imine Hydroiodide and 2-Amino-1-[(3-chloro-4-N,N-dimethylsulfonamidophenyl)methyl]benzimidazole Hydroiodide Following the procedure of Example 2 and replacing 2-phenylethyl bromide with 3-chloro-4-N,N-dimethylsulfonamidophenylmethyliodide, the title compounds are obtained.

EXAMPLE 17

1,3-Dihydro-1,3-bis[2-[6-ethyl-2-(trifluoromethyl)-phenyl]ethyl]-2H-benzimidazol-2-imine Hydrobromide and 2-Amino-1-[2-[6-ethyl-2-(trifluoromethyl)pehnyl]ethyl]benzimidazole Hydrobromide Following the procedure of Example 2 and replacing 2-phenylethyl bromide with 2-[6-ethyl-2-(trifluoromethyl)phenyl]ethylbromide, the title compounds are obtained.

EXAMPLE 18

1,3-Dihydro-1,3-bis[2-(4-N,N-dimethylsulfonamido-3-ethylphenyl)ethyl]-2H-benzimidazol-2-imine Hydrochloride and 2-Amino-1-[2-(4-N,N-dimethylsulfonamido-3-ethylphenyl)-ethyl]benzimidazole Hydrochloride Following the procedure of Example 2 and replacing 2-phenylethyl bromide with 2-(4-N,N-dimethylsulfonamido-3-ethylphenyl)ethyl chloride, the title compounds are obtained.

EXAMPLE 19

1,3-Dihydro-1,3-bis[[2-ethoxy-6-(trifluoromethyl)-phenyl]methyl]-2H-benzimidazol-2-imine Hydrobromide and
2-Amino-1-[[2-ethoxy-6-(trifluoromethyl)phenyl]methyl]benzimidazole Hydrobromide Following the procedure of Example 2 and replacing 2-phenylethyl bromide with 2-ethoxy-6-(trifluoromethyl)phenylmethyl bromide, the title compounds are obtained.

EXAMPLE 20

1,3-Dihydro-1,3-bis[3-(2-s-butoxy-4-N,N-dimethylsulfonamidophenyl)propyl]-2H-benzimidazol-2-imine Hydroiodide and
2-Amino-1-[3-(2-s-butoxy-4-N,N-dimethylsulfonamidophenyl)propyl]benzimidazole Hydroiode Following the procedure of Example 2 and replacing 2-phenylethyl bromide with 3-(2-s-butoxy-4-N,N-dimethylsulfonamidophenyl)propyl iodide, the title compounds are obtained.

EXAMPLE 21

1,3-Dihydro-1,3-bis[2-[4-N,N-dimethylsulfonamido-2-(trifluoromethyl)phenyl]ethyl]-2H-benzimidazol-2-imine Hydrochloride and
2-Amino-1-[2-[4-N,N-dimethylsulfonamido-2-(trifluoromethyl)phenyl]ethyl]benzimidazole Hydrochloride Following the procedure of Example 2 and replacing 2-phenylethyl bromide with 2-[4-N,N-dimethylsulfonamido-2-(trifluoromethyl)phenyl]ethyl chloride, the title compounds are obtained.

EXAMPLE 22

5-Ethoxy-1,3-dihydro-1,3-bis[(o-bromophenyl)methyl]-2H-benzimidazol-2-imine Hydrochloride and
2-Amino-5-ethoxy-1-[(o-bromophenyl)methyl]benzimidazole Hydrochloride Following the procedure of Example 2 and replacing 2-aminobenzimidazole with 2-amino-5-ethoxybenzimidazole and replacing 2-phenylethyl bromide with o-bromophenylmethyl chloride, the title compounds are obtained.

EXAMPLE 23

6-Phenyl-1,3-dihydro-1,3-bis[2-(2,4-dichlorophenyl)ethyl]-2H-benzimidazol-2-imine Hydrobromide and
2-Amino-6-phenyl-1-[2-(2,4-dichlorophenyl)ethyl]benzimidazole Hydrobromide Following the procedure of Example 2 and replacing 2-aminobenzimidazole with 2-amino-6-phenylbenzimidazole and replacing 2-phenylethyl bromide with 2-(2,4-dichlorophenyl)ethyl bromide, the title compounds are obtained.

EXAMPLE 24

7-Chloro-1,3-dihydro-1,3-bis[3-(3-methylphenyl)propyl]-2H-benzimidazole-2-imine Hydrochloride and
2-Amino-7-chloro-1-[3-(3-methylphenyl)propyl]benzimidazole Hydrochloride Following the procedure of Example 2 and replacing 2-aminobenzimidazole with 2-amino-7-chlorobenzimidazole and replacing 2-phenylethyl bromide with 3-(3-methylphenyl)-propyl chloride, the title compounds are obtained.

EXAMPLE 25

5-Benzyl-1,3-dihydro-1,3-bis[4-(3,5-diethylphenyl)butyl]-2H-benzimidazol-2-imine Hydroiodide and
2-Amino-5-benzyl-1-[4-(3,5-diethylphenyl)butyl]benzimidazole Hydroiodide Following the procedure of Example 2 and replacing 2-aminobenzimidazole with 2-amino-5-benzylbenzimidazole and replacing 2-phenylethyl bromide with 4-(3,5-diethylphenyl)butyl iodide, the title compounds are obtained.

EXAMPLE 26

5-(o-Bromophenyl)-1,3-dihydro-1,3-bis[2-[o-(trifluoromethyl)-phenyl]-ethyl]-2H-benzimidazol-2-imine Hydrochloride and
2-Amino-5-(o-bromophenyl)-1-[2-[o-(trifluoromethyl)phenyl]-ethyl]hydrochloride Following the procedure of Example 2 and replacing 2-aminobenzimidazole with 2-amino-5-(o-bromophenyl)benzimidazole and replacing 2-phenylethyl bromide with 2-[o-(trifluoromethyl)phenyl]ethyl choride, the title compounds are obtained.

EXAMPLE 27

5-(2,6-Dichlorophenyl)-1,3-dihydro-1,3-bis[3-(4-N,N-dimethylsulfonamidophenyl)propyl]-2H-benzimidazol-2-imine Hydrochloride and
2-Amino-5-(2,6-dichlorophenyl)-1-[3-(4-N,N-dimethylsulfonamidophenyl)propyl]benzimidazole Hydrochloride Following the procedure of Example 2 and replacing 2-aminobenzimidazole with 2-amino-5-(2,6-dichlorophenyl)-benzimidazole and replacing 2-phenylethyl bromide with 3-(4-N,N-dimethysulfonamidophenyl)-propyl chloride ether, the title compounds are obtained.

EXAMPLE 28

4-(2-Ethyl-3-methoxyphenyl)-1,3-dihydro-1,3-bis[2-(3-methyl-4-propylphenyl)ethyl]-2H-benzimidazol-2-imine Hydrobromide and
2-Amino-4-(2-ethyl-3-methoxyphenyl)-1-[2-(3-methyl-4-propylphenyl)ethyl]benzimidazole Hydrobromide Following the procedure of Example 2 and replacing 2-aminobenzimidazole with 2-amino-4-(2-ethyl-3-methoxyphenyl)-benzimidazole and replacing 2-phenylethyl bromide with 2-(3-methyl-4-propylphenyl)ethyl bromide, the title compounds are obtained.

EXAMPLE 29

7-[3-t-Butyl-5-(trifluoromethyl)phenyl]-1,3-dihydro-1,3-bis[2-(2-bromo-4-N,N-dimethylsulfonamidophenyl)ethyl]-2H-benzimidazol-2-imine Hydroiodide and
2-Amino-7-[3-t-butyl-5-(trifluoromethyl)phenyl]-1-[2-(2-bromo-4-N,N-dimethylsulfonamidophenyl)ethyl]benzimidazole Hydroiodide Following the procedure of Example 2 and replacing 2-aminobenzimidazole with 2-amino-7-[3-t-butyl-5-(trifluoromethyl)phenyl]benzimidazole and replacing 2-phenylethyl bromide with 2-(2-bromo-4-N,N-dimethylsulfonylamidophenyl)ethyl iodide, the title compounds are obtained.

EXAMPLE 30

5,6-Dichloro-1,3-dihydro-1,3-bis[3-(o-bromophenyl)-propyl]-2H-benzimidazol-2-imine Hydrochloride and 2-Amino-5,6-dichloro-1-[3-(o-bromophenyl)propyl]-benzimidazole Hydrochloride Following the procedure of Example 2 and replacing 2-aminobenzimidazole with 2-amino-5,6-dichlorobenzimidazole and replacing 2-phenylethyl bromide with 3-(o-bromophenyl)-propyl chloride, -bromo-title compounds are obtained.

EXAMPLE 31

5,6-Dimethoxy-1,3-dihydro-1,3-bis[2-(2-chloro-3-iodophenyl)-ethyl]-2H-benzimidazol-2-imine Hydrochloride and 2-Amino-5,6-dimethoxy-1-[2-(2-chloro-3-iodophenyl)ethyl]benzimidazole Hydrochloride Following the procedure of Example 2 and replacing 2-aminobenzimidazole with 2-amino-5,6-dimethoxybenzimidazole and replacing 2-phenylethyl bromide with 2-(2-chloro-3-iodophenyl)ethyl chloride, the title compounds are obtained.

EXAMPLE 32

5,6-Dimethyl-1,3-dihydro-1,3-bis[(3,5-dibromophenyl)methyl]-2H-benzimidazol-2-imine Hydrochloride and 2-Amino-5,6-dimethyl-1-[(3,5-dibromophenyl)methyl]benzimidazole Hydrochloride Following the procedure of Example 2 and replacing 2-aminobenzimidazole with 2-amino-5,6-dimethylbenzimidazole and replacing 2-phenylethyl bromide with 3,5-dibromophenylmethyl chloride, the title compounds are obtained.

EXAMPLE 33

5,7-bis(Trifluoromethyl)-1,3-dihydro-1,3-bis[2-(2-bromo-4-fluorophenyl)ethyl]-2H-benzimidazol-2-imine Hydrochloride and 2-Amino-5,7-bis(trifluoromethyl)-1-[2-(2-bromo-4-fluorophenyl)ethyl]benzimidazole Hydrochloride Following the procedure of Example 2 and replacing 2-aminobenzimidazole with 2-amino-5,7-bis(trifluoromethyl)benzimidazole and replacing 2-phenylethyl bromide with 2-(2-bromod-4-fluorophenyl)ethyl chloride, the title compounds are obtained.

EXAMPLE 34

5-Ethoxy-1,3-dihydro-1,3-bis[4-(o-bromophenyl)-butyl]-2H-benzimidazol-2-imine Hydrochloride and 2-Amino-5-ethoxy-1-[4-(o-bromophenyl)butyl]benzimidazole Hydrochloride Following the procedure of Example 2 and replacing 2-aminobenzimidazole with 2-amino-5-ethoxybenzimidazole and replacing 2-phenylethyl bromide with 4-(2-bromophenyl)-butyl chloride, the title compounds are obtained.

EXAMPLE 35

Preparation of Oral Syrup Formulation

| Ingredient | Amount |
|---|---|
| 1,3-Dihydro-1,3-bis[2-(o-bromophenyl)-ethyl]-2H-benzimidazol-2-imine hydrobromide | 1000 mg. |
| Sorbitol solution (70% N.F.) | 40 ml. |
| Sodium benzoate | 150 mg. |
| Saccharin | 15 mg. |
| Red dye (F.D. & C. No. 2) | 10 mg. |
| Cherry flavor | 50 mg. |
| Distilled water, q. s. ad | 100 ml. |

The sorbitol solution is added to 40 ml. of distilled water and the active ingredient is suspended therein. The saccharin, sodium benzoate, flavor and dye are added and dissolved in the above solution. The volume is adjusted to 100 ml. with distilled water.

Other ingredients may replace those listed in the above formulation. For example, a suspending agent such as bentonite magma, tragacanth, carboxymethylcellulose or methylcellulose may be used. Phosphate, citrates or tartrates may be added as buffers. Preservatives may include the parabens, sorbic acid and the like and other flavors and dyes may be used in place of those listed above.

What is claimed is:

1. A method for the treatment of inflammation in mammals, which comprises administering to a mammalian host an anti-inflammatory amount of a compound of the structure

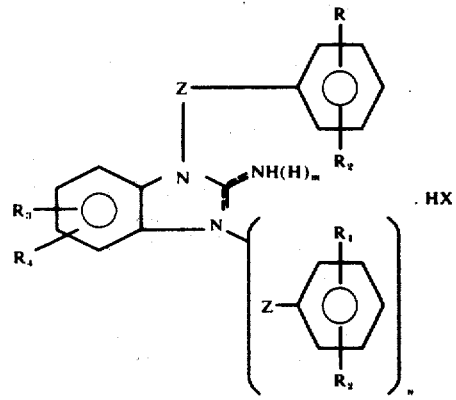

wherein
Z is a straight or branched alkylene group containing 1 to 4 carbons;
$R_1$ and $R_2$ are the same or different and are selected from the group consisting of hydrogen, halo, lower alkyl, lower alkoxy, trifluoromethyl or N,N-dimethylsulfonamido;
$R_3$ and $R_4$ are the same or different and are selected from the group consisting of hydrogen, lower alkyl, lower alkoxy, phenyl, naphthyl, halo, benzyl, phenethyl, or phenyl or naphthyl including an $R_1$ or $R_2$ substituent;
$m$ is 0 or 1 and $n$ is 0 or 1, provided that when $m$ is 0, $n$ is 1 and the === linking N to the ring C is a double bond while the other === is a single bond, and when $m$ is 1, $n$ is 0; the === linking N to the ring C is a single bond while the other === is a double bond; and X is selected from the group consisting of Cl, Br or I.

2. The method of claim 1 wherein $R_1$ and $R_2$ are selected from the group consisting of hydrogen, halo, lower alkyl, lower alkoxy and trifluoromethyl.

3. The method of claim 1 wherein $R_1$ and $R_2$ are selected from the group consisting of hydrogen, halo, lower alkyl and lower alkoxy.

4. The method of claim 1 wherein $R_1$ and $R_2$ are selected from the group consisting of hydrogen, halo, and lower alkyl.

5. The method of claim 1 wherein $R_1$ and $R_2$ are selected from the group consisting of hydrogen or halo.

6. The method of claim 1 wherein $R_3$ and $R_4$ are selected from the group consisting of hydrogen, lower alkyl, and halo.

7. The method of claim 1 wherein Z is —$CH_2$—, —$CH_2CH_2$— or —$CH_2CH_2CH_2$—.

8. A compound having the structure

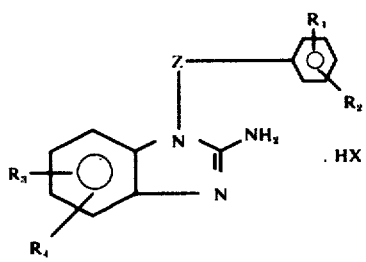

wherein Z is a straight or branched chain alkylene group containing 1 to 4 carbons; $R_1$ is halo and $R_2$ is hydrogen or halo; $R_3$ and $R_4$ are the same or different and are selected from the group consisting of hydrogen, lower alkyl, lower alkoxy, phenyl, naphthyl, halo, benzyl, phenethyl, and phenyl and naphthyl including $R_1$ or $R_2$ groups;

X is Cl, Br or I.

9. The compounds of claim 8 wherein Z is —$CH_2$—, —$CH_2CH_2$— or —$CH_2CH_2CH_2$—, and $R_3$ and $R_4$ are hydrogen.

10. A compound as defined in claim 9 having the name 2-amino-1-benzimidazole hydrobromide.

11. A compound as defined in claim 9 having the name 2-amino-1-(o-bromobenzyl)benzimidazole hydrobromide.

12. A compound as defined in claim 9 having the name 2-amino-1-benzimidazole hydroiodide.

13. A pharmaceutical composition useful in treating inflammation in mammals comprising an effective amount of a compound as defined in claim 8 and a pharmaceutical carrier therefor.

14. A compound having the structure

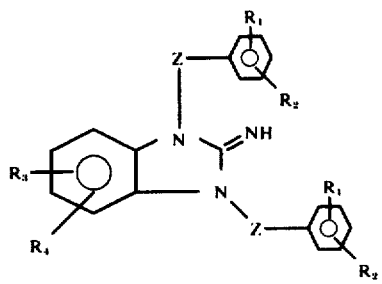

wherein
Z is a straight or branched chain alkylene group containing 1 to 4 carbons;
$R_1$ is halo and $R_2$ is hydrogen or halo;
$R_3$ and $R_4$ are the same or different and are selected from the group consisting of hydrogen, lower alkyl, lower alkoxy, phenyl, naphthyl, halo, benzyl, phenethyl, and phenyl and naphthyl including $R_1$ or $R_2$ substituents;
X is Cl, Br or I.

15. The compounds of claim 14 wherein Z is —$CH_2$—, —$CH_2CH_2$— or —$CH_2CH_2CH_2$—, and $R_3$ and $R_4$ are hydrogen.

16. A compound as defined in claim 15 having the name 1,3-dihydro-1,3-bis-2H-benzimidazol-2-imine hydrobromide.

17. A compound as defined in claim 15 having the name 1,3-dihydro-1,3-bis(o-bromobenzyl)-2H-benzimidazol-2-imine hydrobromide.

18. A compound as defined in claim 15 having the name 1,3-dihydro-1,3-bis-2H-benzimidazol-2-imine hydroiodide.

19. A pharmaceutical composition useful in treating inflammation in mammals comprising an effective amount of a compound as defined in claim 14 and a pharmaceutical carrier therefor.

20. Compounds comprising a mixture of compounds of the structures

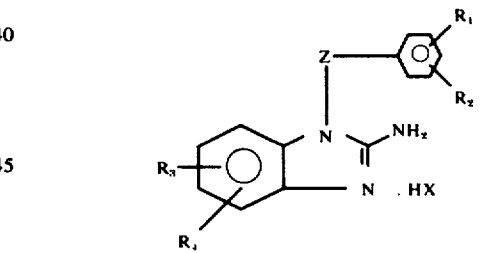

and

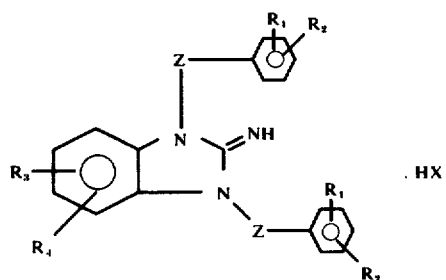

wherein Z is a straight or branched chain alkylene group containing 1 to 4 carbons; $R_1$ is halo and $R_2$ is hydrogen or halo; $R_3$ and $R_4$ are the same or different and are selected from the group consisting of hydrogen, lower alkyl, lower alkoxy, phenyl, naphthyl, halo, benzyl, phenethyl, and phenyl and naphthyl including $R_1$ or $R_2$ groups;
X is Cl, Br or I.

* * * * *

UNITED STATES PATENT AND TRADEMARK OFFICE
CERTIFICATE OF CORRECTION

PATENT NO. : 4,004,016
DATED : January 18, 1977
INVENTOR(S) : Harry L. Yale et al.

It is certified that error appears in the above-identified patent and that said Letters Patent are hereby corrected as shown below:

In the abstract, the structure should read

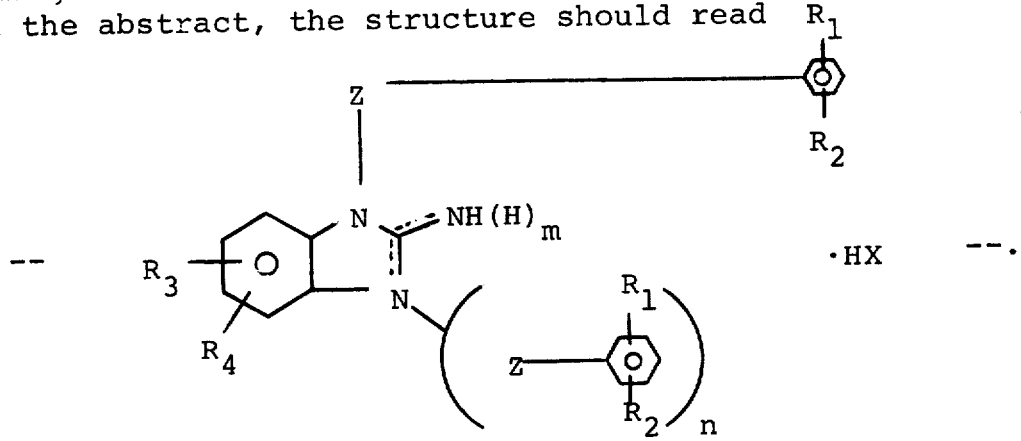

Column 3, line 65, "is" should read --in--.
Column 8, line 51, "pehnyl" should read --phenyl--.
Column 9, line 63, "benzimidazole" should read --benzimidazol--.
Column 11, line 53, "bromod" should read --bromo--.
Column 13, Claim 10, line 2 should read --name 2-amino-1-
   [2-(o-bromophenyl)ethyl]benzimidazole hydrobromide.--.
Column 13, Claim 12, line 2 should read --name 2-amino-1-
   [3-(p-chlorophenyl)propyl]benzimidazole hydroiodide.--
Column 14, Claim 16, line 2 should read --name 1,3-dihydro-
   1,3-bis[2-(o-bromophenyl)ethyl]-2H-benzimidazol-2-imine--.
Column 14, Claim 18, line 2 should read --name 1,3-dihydro-
   1,3-bis[3-(p-chlorophenyl)propyl]-2H-benzimidazol-2-imine--.

Signed and Sealed this

Twelfth Day of April 1977

[SEAL]

Attest:

RUTH C. MASON
Attesting Officer

C. MARSHALL DANN
Commissioner of Patents and Trademarks